(12) United States Patent
Pottier et al.

(10) Patent No.: US 10,064,962 B2
(45) Date of Patent: Sep. 4, 2018

(54) METHOD OF MONITORING THE RELEASE FROM LIPOSOMES OF A PRODUCT OF INTEREST USING SUPERPARAMAGNETIC NANOPARTICLES

(71) Applicants: NANOBIOTIX, Paris (FR); CENTRE NATIONAL DE LA RECHERCHE SCIENTIFIQUE, Paris (FR); UNIVERSITE DE BORDEAUX, Bordeaux (FR)

(72) Inventors: Agnés Pottier, Paris (FR); Laurent Levy, Paris (FR); Marie-Edith Meyre, Paris (FR); Matthieu Germain, Champigny sur Marne (FR); Cyril Lorenzato, Utrecht (NL); Chrit Moonen, Stramproy (NL); Pierre Smirnov, La Rochelle (FR)

(73) Assignees: NANOBIOTIX, Paris (FR); UNIVERSITE DE BORDEAUX, Bordeaux (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 14/886,326

(22) Filed: Oct. 19, 2015

(65) Prior Publication Data
US 2016/0038616 A1    Feb. 11, 2016

Related U.S. Application Data (63) Continuation of application No. 13/981,776, filed as application No. PCT/EP2012/051510 on Jan. 31, 2012, now abandoned.

(60) Provisional application No. 61/437,831, filed on Jan. 31, 2011.

(30) Foreign Application Priority Data

Jan. 31, 2011 (EP) .................................. 11305097

(51) Int. Cl.
| | |
|---|---|
| A61K 9/127 | (2006.01) |
| A61K 49/18 | (2006.01) |
| A61K 9/00 | (2006.01) |
| A61K 9/50 | (2006.01) |
| A61K 9/51 | (2006.01) |
| A61K 41/00 | (2006.01) |
| A61K 31/704 | (2006.01) |
| G01N 24/08 | (2006.01) |
| G01R 33/56 | (2006.01) |

(52) U.S. Cl.
CPC ........ *A61K 49/1812* (2013.01); *A61K 9/0009* (2013.01); *A61K 9/127* (2013.01); *A61K 9/1271* (2013.01); *A61K 9/1278* (2013.01); *A61K 9/5094* (2013.01); *A61K 9/5115* (2013.01); *A61K 31/704* (2013.01); *A61K 41/0028* (2013.01); *G01N 24/088* (2013.01); *G01R 33/5601* (2013.01)

(58) Field of Classification Search
CPC ....................................................... A61K 9/127
See application file for complete search history.

(56) References Cited

U.S. PATENT DOCUMENTS

| | | | |
|---|---|---|---|
| 5,395,619 | A  | 3/1995 | Zalipsky et al. |
| 6,200,598 | B1 | 3/2001 | Needham |
| 6,251,365 | B1 | 6/2001 | Bäuerlein et al. |
| 7,427,393 | B2 | 9/2008 | Takeyama |
| 2006/0099145 | A1 | 5/2006 | Takeyama |
| 2007/0197904 | A1 | 8/2007 | Viglianti et al. |
| 2009/0004258 | A1 | 1/2009 | Yang et al. |

(Continued)

FOREIGN PATENT DOCUMENTS

| | | |
|---|---|---|
| EP | 2067485 | 6/2009 |
| JP | 2001-527534 | 12/2001 |
| WO | WO 2006/051732 | 5/2006 |

(Continued)

OTHER PUBLICATIONS

Radu et al. (2015). "Exposure to Iron Oxide Nanoparticles Coated with Phospholipid-Based Polymeric Micelles Induces Biochemical and Histopathological Pulmonary Changes in Mice." International Journal of Molecular Sciences, 16: 29417-29435.*

(Continued)

*Primary Examiner* — Brian M Gulledge
(74) *Attorney, Agent, or Firm* — Saliwanchik, Lloyd & Eisenschenk (57) ABSTRACT

The invention pertains to a method of monitoring the membrane permeabilization of a liposome and the incidental release of a compound of interest. The method utilizes liposomes comprising a thermosensitive lipidic membrane encapsulating the product of interest and superparamagnetic nanoparticles having the electrostatic surface charge below −20 mV or above +20 mV when measured in an aqueous medium at physiological pH. In one embodiment, the method comprises the steps of: a) measuring relaxation time (T2*); b) heating the liposome at Tm or above Tm; c) measuring T2* after step b); d) obtaining the transverse relaxivity ($r_{2*}$) values from the T2* values obtained from step a) and step c); and e) determining the ratio of $r_{2*}$ before and after the heating step b). A ratio above 1.5 indicates the liposome membrane permeabilization and the incidental release of the product of interest.

18 Claims, 6 Drawing Sheets
(3 of 6 Drawing Sheet(s) Filed in Color)

(56) References Cited

U.S. PATENT DOCUMENTS

2014/0056813 A1    2/2014    Pottier et al.

FOREIGN PATENT DOCUMENTS

| WO | WO 2008/033031 |   | 3/2008 |   |          |
|----|----------------|---|--------|---|----------|
| WO | WO 2008/035985 |   | 3/2008 |   |          |
| WO | WO 2010/0299469 | * | 3/2010 | ............ | A61K 9/127 |
| WO | WO 2012/104275 |   | 8/2012 |   |          |

OTHER PUBLICATIONS

Kato et al. (2009). "Monitoring of Release of Cargo From Nanocarriers by MRI/MR Spectroscopy (MRS): Significance of T2/T2* Effect of Iron Particles." Magnetic Resonance in Medicine, 61: 1059-1065.*

Salomir et al. (2005). "Local Delivery of Magnetic Resonance (MR) Contrast Agent in Kidney Using Thermosensitive Liposomes and MR Imaging-Guided Local Hyperthermia: A Feasibility Study in Vivo." Journal of Magnetic Resonance Imaging, 22: 534-540.*

Taglienti, A., et al., "Kinetics of drug release from a hyaluronan-steroid conjugate investigated by NMR spectroscopy," *Carbohydrate Research*, 2009, vol. 344, pp. 245-249.

Aime, S. et al. "Gd-Loaded Liposomes as $T_1$, Susceptibility, and CEST Agents, All in One" *Journal of the American Chemical Society*, 2007, pp. 2430-2431, vol. 129, No. 9.

Arruebo, M. et al. "Magnetic nanoparticles for drug delivery" *Nano Today*, Jun. 2007, pp. 22-32, vol. 2, No. 3.

Written Opinion in International Application No. PCT/EP2012/051510, dated Aug. 30, 2012, pp. 1-8.

Mahmoudi, M. et al. "Superparamagnetic iron oxide nanoparticles (SPIONs): Development, surface modification and applications in chemotherapy" *Advanced Drug Delivery Reviews*, 2011, pp. 24-46, vol. 63.

Bakandritsos, A. et al. "Synthesis and Characterization of Iron Oxide Nanoparticles Encapsulated in Lipid Membranes" *Journal of Biomedical Nanotechnology*, 2008, pp. 313-318, vol. 4.

Fortin-Ripoche, J.-P. et al. "Magnetic Targeting of Magnetoliposomes to Solid Tumors with MR Imaging Monitoring in Mice: Feasibility" *Radiology*, May 2006, pp. 415-424, vol. 239, No. 2.

Written Opinion in International Application No. PCT/EP2012/051507, dated Sep. 11, 2012, pp. 1-7.

Lorenzato, C. et al. "MRI contrast variation of thermosensitive magnetoliposomes triggered by focused ultrasound: a tool for image-guided local drug delivery" *Contrast Media Mol. Imaging*, 2013, pp. 185-192, vol. 8.

Golovko, D. M. et al. "Accelerated stem cell labeling with ferucarbotran and protamine" *Eur Radiol.*, 2010, pp. 640-648, vol. 20.

Motosugi, U. et al. "II the Latest Trend of MRI Contrast Agent, Emergence of liver-specific contrast agent for possible bolus injection, 1. SPIO Formulation" *Innervision*, (17-9), 2002, pp. 23-25.

Gao, Z. et al, "Diacyllipid-Polymer Micelles as Nanocarriers for Poorly Soluble Anticancer Drugs" *Nano Letters*, 2002, pp. 979-982, vol. 2, No. 9.

Cinteza, L. O. et al. "Diacyllipid Micelle-Based Nanocarrier for Magnetically Guided Delivery of Drugs in Photodynamic Therapy" *Molecular Pharmaceutics*, Feb. 14, 2006, pp. 415-423, vol. 3, No. 4.

Zhao, B. et al. "Nanotoxicity comparison of four amphiphilic polymeric micelles with similar hydrophilic or hydrophobic structure" *Particle and Fibre Toxicology*, 2013, pp. 1-16, vol. 10, No. 47.

\* cited by examiner

METHOD OF MONITORING THE RELEASE FROM LIPOSOMES OF A PRODUCT OF INTEREST USING SUPERPARAMAGNETIC NANOPARTICLES

CROSS-REFERENCE TO RELATED APPLICATIONS

This application is a continuation of U.S. application Ser. No. 13/981,776, filed Apr. 15, 2014, which is the U.S. national stage application of International Patent Application No. PCT/EP2012/051510, filed Jan. 31, 2012, which claims the benefit of U.S. Provisional Application Ser. No. 61/437,831, filed Jan. 31, 2011.

FIELD OF THE INVENTION

The present invention is to be used in the health sector, in particular in human health.

The methods and compositions disclosed herein generally relate to employing magnetic resonance techniques to monitor the deliver of a compound of interest in vivo. More particularly, the disclosure relates to the use of superparamagnetic nanoparticles, the electrostatic surface charge of which is below −20 mV or above +20 mV when measured in an aqueous medium at physiological pH to monitor the membrane permeabilization of thermosensitive liposomes and the incidental release, to a desired site in vivo, of a compound of interest.

BACKGROUND

Medical diagnostic imaging has evolved as an important non-invasive tool for the evaluation of pathological and physiological processes. Presently, nuclear magnetic resonance imaging (MRI) is one of the most widely used imaging modalities, demonstrating many advantages over other techniques like computed tomography. The innocuousness of the applied magnetic field typically used for clinical diagnosis results in its safe use. Proton MRI is based on the principle that the concentration and relaxation characteristics of protons in tissues and organs, when submitted to a static magnetic field, can influence the intensity of a magnetic resonance image. As a result, this technique brings a high contrast resolution, which allows for morphological imaging thanks to contrast tissue differentiation due to differences in proton density of the different tissues (depending on fat or water content). A functional imaging of certain organs can also be performed, i.e., blood oxygenation, or cerebral area activation under sensorial stimuli. MRI also demonstrates a high spatial resolution, as cellular imaging is envisaged with a strong magnetic field and no depth limitations. Although MRI can be performed without the administration of contrast agents, the ability of many contrast enhancement agents to enhance the visualization of internal tissues and organs has resulted in its widespread use. Contrast enhancement agents that are useful for proton MRI are responsible for a change in the relaxation characteristics of protons, which can result in image enhancement and improved soft-tissue differentiation.

The use, as a drug delivery vehicle, of thermosensitive liposomes losing their structural integrity within a given temperature range is a promising approach to targeting a tumor or other tissue, but so far no efficient liposomal MRI contrast agents have been proposed.

US 2004/0101969 describes a method of monitoring the localisation and distribution of a compound of interest released from an envirosensitive liposome, using a molecular compound, $MnSO_4$, as a contrast agent.

WO 2008/035985 describes a trackable particulate material for drug delivery comprising a matrix or membrane material, a drug, an internal T1 magnetic resonance metal chelate contrast agent and an external T1 magnetic resonance metal chelate contrast agent, wherein the internal T1 agent is shielded from bulk water and the external T1 agent is exposed to bulk water.

EP 2067485 describes thermosensitive liposomes for drug delivery which comprise a paramagnetic metal compound. The paramagnetic metal compound may be a metallic nanoparticle. Preferably, the paramagnetic metal compound comprises a chelating structure allowing the metal to interact with water or with another suitable source of protons as a chemical exchange-dependent saturation transfer (CEST) contrast agent.

These documents all refer to contrast agents which are T1 magnetic resonance paramagnetic molecular compounds and offer only a limited sensitivity when measured in vivo. As a result, relatively large, and possibly toxic, doses of such contrast agents are to be administered to a given subject. This and other problems are addressed by the compositions and methods herein disclosed.

WO 2008/033031 describes a trackable MRI drug delivery particle comprising two distinct chemical contrast agents, one of them (T1 agent) exhibiting a T1 signal used to monitor drug release, and the other one (T2* agent) exhibiting a T2* signal. This document does not suggest using the T2* agent to monitor drug release.

US2009/004258 describes thermosensitive liposomes encapsulating iron oxide nanoparticles and carbofluoresceine (CF), CF being used as a drug model. Nanoparticles are capable of generating heat when activated by an alternative magnetic field, thereby allowing permeabilization of the membrane towards CF. In US2009/004258, monitoring of the CF's release is performed by fluorescence detection.

The inventors herein provide an advantageous method offering superior sensitivity, relative to the currently available methods. This method in particular uses low doses of non-toxic charged superparamagnetic nanoparticles and allows the monitoring of liposome delivery to a target site and also, surprisingly, the efficient monitoring of the product of interest's release from said liposomes.

SUMMARY OF THE INVENTION

The inventors herein provide a method of monitoring the liposome membrane permeabilization and the incidental release of a product of interest, the liposome comprising a thermosensitive lipidic membrane encapsulating superparamagnetic nanoparticles, the electrostatic surface charge of which is below −20 mV or above +20 mV when measured in an aqueous medium at physiological pH, the method comprising, in a first embodiment, the following steps of:
a) measuring T2*,
b) heating the liposome at Tm or above Tm,
c) measuring T2* after step b),
d) obtaining the $r_{2*}$ values from the T2* values obtained from step a) and step c), and
e) determining the ratio of $r_{2*}$ before the heating step at Tm or above Tm/$r_{2*}$ after the heating step at Tm or above Tm, a ratio above 1.5 being indicative of the liposome membrane permeabilization and of the incidental release of the product of interest, thereby monitoring the liposome membrane permeabilization.

In a particular embodiment, the method further comprises measuring T2*, or T2 and T2*, during the heating step b).

In a second embodiment, the method comprises the following steps of:
a) measuring T2* and T1,
b) heating the liposome at Tm or above Tm,
c) measuring T2* and T1 after step b),
d) obtaining $r_{2*}$ and $r_1$ values from the T2* and T1 values obtained from steps a) and c), and
e) determining the ratio of $r_{2*}/r_1$ before and after the heating step at Tm or above Tm, a ratio of $r_{2*}/r_1$ before the heating step b) and of $r_{2*}/r_1$ after the heating step b) above 2 being indicative of the liposome membrane permeabilization and of the incidental release of the product of interest, thereby monitoring the liposome membrane permeabilization.

In a particular embodiment, the method further comprises measuring T2* and T1, and optionally T2, during the heating step b).

The inventors herein surprisingly demonstrate that the thermosensitive liposome membrane permeabilization, upon heating, and the incidental release of a product of interest result in a variation of the magnetic resonance imaging (MRI) signal, allowed by the superparamagnetic nanoparticles encapsulated in the liposome, which is of high value and easily measurable.

The inventors herein provide a thermosensitive liposome comprising a thermosensitive lipidic membrane encapsulating superparamagnetic nanoparticles, the electrostatic surface charge of the nanoparticles being below −20 mV or above +20 mV when measured in an aqueous medium at physiological pH, and the nanoparticles being preferably usable as a diagnostic or monitoring agent. Typically, such a liposome is for use in a method, according to the present invention and as herein described, of monitoring the liposome membrane permeabilization and the incidental release of a product of interest.

In a particular embodiment, the thermosensitive liposome is a liposome comprising a thermosensitive lipidic membrane encapsulating nanoparticles, the nanoparticles being usable as a therapeutic or diagnostic agent, each nanoparticle i) comprising an inorganic core, the largest dimension of which is less than about 100 nm, and ii) being fully coated with an agent responsible for the presence of an electrostatic charge below −20 mV or above +20 mV at the surface of the nanoparticle, the electrostatic charge being determined by zeta potential measurements in an aqueous medium between pH 6 and 8, for a concentration of nanoparticles in suspension varying between 0.2 and 8 g/L.

In another aspect, the present disclosure provides kits comprising any one or more of the herein-described products, i.e., thermosensitive liposomes and compositions, together with a labeling notice providing instructions for using the product(s) in the context of the herein-described methods.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 2 shows the elution profile for iron oxide-containing liposomes determined by quantification of magnetic nanoparticles by UV-visible spectroscopy (Cary 100 Varian spectrometer) via a colorimetric reaction between ferrous ions and phenanthroline. The concentration of iron oxide in the liposomes ranges from 1 to 2.5 g/L.

FIG. 3 shows the release kinetic profile of doxorubicin (DOX)-loaded iron oxide-containing thermosensitive liposomes (TSL), determined by fluorescence measurements. Samples were aged in a medium comprising Phosphate Buffer Saline 1× (PBS 1×) and Fetal Bovine Serum (FBS) (volume ratio 1:1), at 37° C., 41° C., 43° C., and 45° C. Heating is performed via a water bath.

FIG. 4A shows longitudinal ($r_1$) relaxivities of thermosensitive liposomes (TSL) and non-thermosensitive liposomes (NTSL), both loaded with 5 nm-sized iron oxide nanoparticles, and free nanoparticles (free NP) at 1.5 Tesla, before (black) and after (grey) heating at 45° C. Heating is performed via a water bath.

FIG. 4B shows transverse ($r_{2*}$) relaxivities of thermosensitive liposomes (TSL) and non-thermosensitive liposomes (NTSL), both loaded with 5 nm-sized iron oxide nanoparticles, and free nanoparticles (free NP) at 1.5 Tesla, before (black) and after (grey) heating at 45° C. Heating is performed via a water bath.

FIG. 5 shows the MR images at 1.5 Tesla of solutions of iron oxide nanoparticles encapsulated within thermosensitive (TSL) and non-thermosensitive liposomes (NTSL), and free nanoparticles (free NP), at 37° C. and 45° C. for the following dilutions: 40, 20, 10 and 5 μg/mL in iron oxide. Gadolinium-based chelate Dotarem, 0.5 mM was used as a control (control).

FIG. 6 shows MR images and T2*-mapping of iron oxide nanoparticles encapsulated in thermosensitive liposomes (TSL), before and after heating with a HIFU device. Red arrows show changes in T2* at the HIFU focal point corresponding to permeabilization of the thermosensitive liposomes upon heating at or above Tm.

DETAILED DESCRIPTION OF THE INVENTION

By applying a pulse of radiofrequency energy at the precise precession (Larmor) frequency of the magnetic moment of a sample, precessing nuclei in the lower energy state are converted to precessing nuclei in the higher energy state, thereby achieving resonance. When the radiofrequency pulse is turned off, the excited nuclei relax to achieve the initial equilibrium state. This relaxation can be achieved in two ways. In the first process, termed spin-lattice relaxation (also longitudinal or T1 relaxation), the excited nucleus gives off its energy to the surrounding environment (lattice) at a particular rate characterized by a time-constant T1, and in the second process, termed spin-spin relaxation (also transverse or T2 relaxation), a nucleus in the high energy state exchanges energy with a nucleus in the low energy state at a particular rate characterized by a time-constant T2. The values for T1 and T2 depend upon the chemical and magnetic environment in which a particular nucleus is situated, and different structures and tissues within the body have different T1 and T2 values (Tilcock et al., Adv Drug Delivery Reviews, 1999, 37:33-51).

It is principally the relative magnitude of these two relaxation processes that generates the contrast between different tissues in the MR image and, depending upon the details of the pulse sequence used (i.e., the echo time TE, which is the time between the pulse and the top of the echo, and the repetition time TR, which is the time between pulses), the image can be weighted to show mainly differences in T1 or T2.

Water proton relaxation processes can be "catalyzed" by the use of magnetic resonance (MR) contrast agents, thus shortening the longitudinal (T1) and transverse (T2) relaxation times and, therefore, increasing the intensity of the MR signal in the regions where they are distributed (S. Aime, et al., Biopolymers, 2002, 66:419-428). The efficacy of an MR contrast agent is commonly evaluated in terms of its impact on the proton relaxation rates, or relaxivities, $r_1$ and $r_2$. They are determined from the linear relationship: $1/T_{i,meas} = 1/T_{i,medium} + r_i \times [CA]$ (with i=1 or i=2), where $T_{i,meas}$ is the relaxation time measured, $T_{i,\,medium}$ is the relaxation time of the region of interest without the contrast agent, and [CA] refers to the contrast agent concentration (Martina el al., J. Am. Chem. Soc., 2005, 127:10676-10685). Relaxivities are then expressed in $s^{-1}$ per contrast agent concentration. Contrast agents increase both longitudinal and transverse relaxivities but to varying degrees, depending on their nature, the applied magnetic field and the pulse sequence used ("T1-weighted" or "T2-weighted" images).

There are two main classes of contrast agents for MRI: paramagnetic complexes and superparamagnetic iron oxide nanoparticles.

The first class includes mainly chelates of ions presenting a high number of unpaired spins, i.e., Mn(II), Mn(III) and Gd(III) ions, conferring to them a paramagnetic behavior. Gadolinium-based agents are the most commonly used. Paramagnetic agents increase $r_1$ and $r_2$ by similar amounts, but are best visualized using T1-weighted images since the percentage change in $r_1$ in the tissue is much greater than that in $r_2$ (Koslowska et al., Adv. Drug Deliv. Rev., 2009, 61:1402-1411).

The second class of contrast agents is constituted of superparamagnetic iron oxide nanoparticles, iron oxide being maghemite ($\gamma$-$Fe_2O_3$) or magnetite ($Fe_3O_4$) crystalline structure (De Cuyper et al., Methods in Enzymology, 2003, 373:175-198). Superparamagnetism occurs when the size of the crystals is smaller than ferromagnetic domains (approximately 30 nm) and, consequently, they do not show any magnetic remanence (i.e., restoration of the induced magnetization to zero upon removal of the external magnetic field), unlike ferromagnetic materials. Each crystal is then considered to be a fully magnetized single magnetic monodomain, and can be considered to be a monomagnet which is a direct consequence of the spinel structure of the crystal, allowing strong magnetic coupling and consequently perfect alignment of the individual magnetic spins (Corot et al., Adv. Drug Deliv. Rev., 2006, 58:1471-1504).

Superparamagnetic contrast agents generally lead to a much larger increase in $r_2$ than in $r_1$ and are best seen with T2-weighted scans (Koslowska et al., Adv. Drug Deliv. Rev., 2009, 61:1402-1411). This predominant effect on the T2 relaxation time does not prevent the use of the properties of these agents on the T1 relaxation time when appropriate imaging sequences are chosen (C. Chambon et al., Magn. Reson. Imaging, 1993, 11:509-519; E. Canet et al., Magn. Reson. Imaging, 1993, 11:1139-1145).

Due to their high magnetic susceptibility, superparamagnetic nanoparticles also generate local magnetic field inhomogeneities, thus leading to a loss of phase coherence among spins oriented at an angle to the static magnetic field. This phenomenon results in another type of relaxation time, T2*, which is commonly due to a combination of magnetic field inhomogeneities and spin-spin transverse relaxation, with the result of rapid loss in transverse magnetization. T2* is defined as: $1/T2^* = 1/T2 + 1/T_{inhomogeneities} = 1/T2 + \gamma \Delta B_0$, where $\gamma$ represents gyromagnetic ratio, and $\Delta B_0$ the difference in strength of the locally varying field. Superparamagnetic contrast agents are then highly sensitive to T2*-weighted scans.

Paramagnetic agents directly affect water protons in their close vicinity and are highly dependent on local water flux. Hence, the influence of these agents is very local and they should ideally be in contact with water with adequate exchange rates. In contrast, superparamagnetic agents affect the magnetic field independent of their environment and thus their influence in terms of contrast extends well beyond their immediate surroundings (G. M. Lanza et al., J. Nucl. Cardiol., 2004, 11:733-743). On conventional spin-echo MR images, the presence of T2 (superparamagnetic) agents leads to a dark (hypointense) appearance of tissue, whereas T1 agents cause the opposite (hyperintensity).

The thermosensitive liposomes used in the context of the present invention can be administered to a subject by different routes such as local (intra-tumoral (IT), for example), subcutaneous, intravenous (IV), intradermal, intra-arterial, airways (inhalation), intraperitoneal, intramuscular and oral routes (per os).

As used herein, the term "subject" means any organism. The term need not refer exclusively to a human being, which is one example of a subject, but can also refer to animals, in particular warm-blooded vertebrates, typically mammals, and even tissue cultures.

The inventors herein provide a method of monitoring, in particular in vivo, the liposome membrane permeabilization and the incidental release of a product of interest, the liposome comprising a thermosensitive lipidic membrane encapsulating superparamagnetic nanoparticles, the "electrostatic surface charge" (also herein identified as "charge" or "surface charge") of which is below −20 mV or above +20 mV when measured in an aqueous medium at physiological pH (between 6 and 8).

In a typical embodiment of the present invention, the method comprises the following steps of:
a) measuring T2*,
b) heating the liposome at Tm or above Tm,
c) measuring T2* after step b),
d) obtaining the $r_{2*}$ values from the T2* values obtained from step a) and step c), and
e) determining the ratio of $r_{2*}$ before the heating step at Tm or above Tm/$r_{2*}$ after the heating step at Tm or above Tm, a ratio above 1.5 being indicative of the liposome membrane permeabilization and of the incidental release of the product of interest, thereby monitoring the liposome membrane permeabilization.

As mentioned above, the $r_{2*}$ ratio varies in response to the liposome membrane permeabilization, i.e., in response to the product of interest's release from the liposomes. More specifically, the $r_{2*}$ ratio varies from 1.2 up to 10, and preferably the $r_{2*}$ ratio is above 1.5.

In a particular embodiment, the method further comprises measuring T2*, or T2 and T2*, during the heating step b).

In a second embodiment, the method comprises the following steps of:
a) measuring T2* and T1,
b) heating the liposome at Tm or above Tm,
c) measuring T2* and T1 after step b),
d) obtaining $r_{2*}$ and $r_1$ values from, the T2* and T1 values obtained from steps a) and c), and
e) determining the ratio of $r_{2*}/r_1$ before and after the heating step at Tm or above Tm, a ratio of $r_{2*}/r_1$ before the heating step b) and of $r_{2*}/r_1$ after the heating step b) above 2 being indicative of the liposome membrane permeabilization and of the incidental release of the product of interest, thereby monitoring the liposome membrane permeabilization.

As mentioned above, the $r_{2*}/r_1$ ratio varies in response to the liposome membrane permeabilization, i.e., in response to the product of interest's release from the liposomes. More specifically, the $r_{2*}/r_1$ ratio varies from 1.2 up to 20, and preferably the $r_{2*}/r_1$ is above 2, more preferably above 5.

In a particular embodiment, the method further comprises measuring T2* and T1, and optionally T2, during the heating step b).

The term "measuring" refers to a complete acquisition or to a real-time acquisition of T2, T2* or T1 in the context of real-time imaging techniques.

Typically, when performed in vivo, the heating step b) at Tm or above Tm of the herein-described methods is performed locally in order to monitor the liposome membrane permeabilization and the incidental release of a product of interest in a specific area (corresponding to the heat-treated area) of a subject. Such a locally performed method allows the assessment of spatial distribution of the released product.

The inventors herein provide a thermosensitive liposome with a Tm (gel-to-liquid crystalline phase transition temperature). This liposome comprises a thermosensitive lipidic membrane encapsulating nanoparticles, the electrostatic surface charge of which is below −20 mV or above +20 mV when measured in an aqueous medium at physiological pH (typically between pH 6 and pH 8). These nanoparticles are usable as a diagnostic agent to monitor the delivery of thermosensitive liposomes to a target site and the efficient monitoring of the product of interest's release from said thermosensitive liposomes when said liposomes are activated by heat. Preferably, the inventors thus herein provide a liposome comprising a thermosensitive lipidic membrane encapsulating nanoparticles, the electrostatic surface charge of which is below −20 mV or above +20 mV when measured in an aqueous medium between pH 6 and 8, for use in a method of monitoring the liposome membrane permeabilization and the incidental release of a product of interest (the product of interest being originally present in addition to the nanoparticles in said liposome). As further explained below, the electrostatic charge is typically determined by zeta potential measurements in an aqueous medium between pH 6 and 8, for a concentration of nanoparticles in suspension varying between 0.2 and 8 g/L.

The term "liposome" refers to a spherical vesicle composed of at least one bilayer of amphipathic molecules which forms a membrane separating an intravesicular medium from an external medium. The intravesicular medium constitutes the internal aqueous core of the liposome. Hydrophilic molecules or components can be encapsulated inside the internal aqueous core of the liposome via active methods of encapsulation known by the skilled person and further herein below described. Hydrophobic molecules or components can be entrapped inside the membrane.

The amphipathic molecules constituting the bilayer are lipids, more particularly phospholipids. The amphipathic characteristic of phospholipid molecules lies in the presence of a hydrophilic head, constituted by a phosphate group and a glycerol group, and a hydrophobic tail, constituted by one or two fatty acids.

In an aqueous medium, phospholipids tend to self-assemble to minimize contact of the fatty acyl chains with water, and they tend to adopt different types of assembly (micelles, lamellar phase, etc.) according to their chemical structure. More particularly, phosphatidylcholines are known to form a lamellar phase consisting of stacked bilayers undergoing a "spontaneous" curvature and finally forming vesicles (Lasic et at, Adv. Colloid. Interf. Sci., 2001, 89-90:337-349). The phospholipidic lamellar phase constitutes a thermotropic liquid crystal. This means that the ordering degree of the amphipathic molecules depends on the temperature. Indeed, a phospholipidic bilayer demonstrates a main phase transition temperature $T_m$ (for temperature of "melting") corresponding to a transition between the "gel-like" lamellar phase $L_\beta$ to the "fluid-like" lamellar phase $L_\alpha$. In the "gel" phase, strong hydrophobic interactions between the carbonated chains of the fatty acids provoke a crystalline ordering of phospholipid molecules; the bilayer is only permeable to small ions. In the "fluid" phase, the hydrophobic tails are moving due to the thermal motion which causes a loss of ordering of the phospholipid molecules and leads to a "liquid crystalline" phase: the bilayer becomes permeable to molecules such as a drug.

The "gel-to-liquid crystalline" phase transition temperature $T_m$ depends on the chemical structure of the phospholipid molecule: hydrocarbon chain length, unsaturation, asymmetry and branching of fatty acids, type of chain-glycerol linkage (ester, ether, amide), position of chain attachment to the glycerol backbone (1,2- vs 1,3-) and head group modification.

In the case of phosphatidylcholines, the structure and conformation of fatty acyl chains is of particular relevance (Koynova et al., Biochim. Biophys. Acta, 1998, 1376:91-145).

Increasing the chain length of fatty acids increases the main phase transition temperature. For example, it was shown that for saturated diacyl phosphatidylcholines with chain lengths ranging from 9 to 24 carbon atoms, $T_m$ is linearly dependent on 1/n (n being the number of carbon atoms in the fatty acyl chains), with $T_m$ increasing from, e.g., 41° C. for n=16 to 80° C. for n=24.

The effect of unsaturation on the main gel-to-liquid crystalline phase transition temperature depends on the conformation (cis or trans type), the position in the fatty acyl chains and the number of double bonds. For example, introducing a single site of unsaturation of the cis type on the sn-2 chain only and in both chains of a phosphatidylcholine comprising 18 carbons can have the effect of lowering the chain melting transition temperature by 50° C. (from 54.5° C. to 3.8° C.) and 75° C. (from 54.5° C. to −21° C.), respectively. In contrast, when the double bond is of trans type, the effect is considerably lessened. Further, $T_m$ depends critically on the position of the cis-double bond. Specifically, $T_m$ is minimized when the double bond is located near the geometric center of the hydrocarbon chain, and progressively increases as the double bond migrates toward either end of the chain. These dependencies apply when the double bond is present in the sn-2 chain only or in both chains of the phosphatidylcholine. Concerning the influence of the number of double bonds, it was shown that by increasing the number of cis-unsaturation $T_m$ is decreased. For example, when two or three sites of cis-unsaturation are introduced into both acyl chains of a phosphatidylcholine comprising 18 carbons, the chain melting transition temperature is lowered by an impressive 109° C. (from 54.5° C. to −55.1° C.) and 116° C. (from 54.5° C. to −61.5° C.), respectively (Koynova et al., Biochim. Biophys. Acta, 1998, 1376:91-145).

Mixed-chain phosphatidylcholines present different hydrocarbon chain lengths at the sn-1 and sn-2 positions. Empirical equations have been derived that allow for accurate prediction of the transition temperatures of related phosphatidylcholines of defined structure. A normalized chain-length inequivalence parameter, $\Delta C/CL$, has been described, where $\Delta C$ ($=|n_1-n_2+1.5|$) is the effective chain-length difference, and $n_1$ and $n_2$ are the number of carbons in the chains at the sn-1 and sn-2 positions of the glycerol backbone, respectively. CL is the effective length of the longer of the two chains. For phosphatidylcholines demonstrating the same number of total carbon atoms constituting the two chains ($n_1+n_2$=constant), the chain melting temperature decreases monotically when the chain length inequivalence parameter $\Delta C/CL$ is increased to about 0.4. When $\Delta C/CL$ goes above ca. 0.4, packing perturbation, caused by the methyl ends of the acyl chains, becomes so overwhelming that the asymmetric phosphatidylcholine molecules adopt a new packing arrangement, referred to as mixed interdigitation. Upon this rearrangement, $T_m$ increases with chain length asymmetry.

For drug delivery purposes, a sterol component may be included to confer the liposome suitable physicochemical and biological behavior. Such a sterol component may be selected from cholesterol or its derivative, e.g., ergosterol or cholesterol hemisuccinate, but is preferably cholesterol.

Cholesterol is often used in lipidic formulation of liposomes because it is generally recognized that the presence of cholesterol decreases their permeability and protects them from the destabilizing effect of plasma or serum proteins.

The cholesterol molecule contains three well-distinguished regions: a small polar hydroxyl group, a rigid plate-like steroid ring, and an alkyl chain tail. When cholesterol intercalates into the membrane, its polar hydroxyl groups positioned near the middle of the glycerol backbone region of the phosphatidylcholine molecule (Kepczynski M. et al., Chemistry and Physics of Lipids, 2008, 155:7-15). Incorporation of modifiers such as cholesterol into the lipid bilayers greatly changes the structural or physical properties of the liposomal membrane, such as its organization, free volume, thickness, fluidity (viscosity) and polarity (hydrophobicity).

The bilayer's viscosity depends on the position of cholesterol within the bilayer, which influences the free volume of the membrane, and on the temperature. The effect of cholesterol on the bilayer's microviscosity is rather complex. It is well-known that cholesterol increases the apparent microviscosities (reduces fluidity) of membranes in liquid phase (Cournia et al., J. Phys. Chem. B, 2007, 111:1786-1801).

Papahadjopoulos et al. showed that the protective effect of cholesterol for liposomes depends on the physical state, i.e., "gel" or "fluid", of the lipidic membrane when in contact with serum or plasma. In the gel state, the presence of cholesterol affects the ordering parameter of the phospholipid acyl chains within the bilayer and enhances the release of entrapped molecules. In the fluid state, cholesterol stabilizes the liposomes and prevents leakage of encapsulated material (Papahadjopoulos et al., Pharm. Research, 1995, 12(10): 1407-1416).

Upon addition of cholesterol in a concentration above 25 molar percentage (mol %), there is a dramatic influence on the gel-to-liquid crystal lipid-phase transition. A new thermodynamically stable region of coexistence between the liquid-disordered (fluid) and solid-ordered (gel) phase is described: the liquid-ordered phase (Cournia et al., J. Phys. Chem. B, 2007, 111:1786-1801; Polozov et al., Biophysical Journal, 2006, 90:2051-2061). This new phase is characterized by a fluidity which is intermediate between the fluidity of the gel phase and the fluidity of the fluid phase formed by the pure lipids. Recently, it has been proposed that the liquid-ordered phase is formed when cholesterol associates with saturated, high-melting lipids, such as dipalmitoylphosphatidylcholine (DPPC) and sphingomyelin, to create dynamic complexes in model membranes, called "lipid-rafts". Cholesterol promotes a phase separation in model membranes where cholesterol-rich and cholesterol-poor microdomains are formed (Radhakrishnan et al., Proc. Natl. Acad. Sci., 2000, 97:12422-12427; McConnell et al., Biochim. Biophys. Acta, 2003, 1610:159-173). Indeed, Gaber et al. (Pharm. Research, 1995, 12(10):1407-1416) showed that two lipidic formulations containing 33 mol % of cholesterol dipalmitoylphosphatidylcholine (DPPC), hydrogenated soybean phosphatidylcholine (HSPC) and cholesterol, in the molar ratio of 100:50:75 and 50:50:50 respectively, do not present a phase transition temperature between 30° C. and 65° C., as demonstrated by differential scanning calorimetry measurements. Liposomes with such a formulation are called "non-thermosensitive" liposomes.

Typical "thermosensitive" liposomes usable in the context of the present invention (i.e., liposomes with a main phase transition temperature $T_m$ typically comprised between 39° C. and 55° C., preferably between 39° C. and 50° C., even more preferably between 39° C. and 45° C.) comprise at least a phosphatidylcholine.

The phosphatidylcholine may be selected from dipalmitoylphosphatidylcholine (DPPC), distearylphosphatidylcholine (DSPC), hydrogenated soybean phosphatidylcholine (HSPC), monopalmitoylphosphatidylcholine (MPPC), monostearylphosphatidylcholine (MSPC) and any mixture thereof.

In a preferred embodiment the thermosensitive liposome further comprises distearylphosphatidylethanolamine (DSPE), and distearylphosphatidylethanolamine (DSPE)-methoxypoly ethylene glycol (PEG) (DSPE-PEG).

In a preferred embodiment, cholesterol is added in a molar ratio inferior to 25 mol %.

A preferred thermosensitive lipidic membrane comprises dipalmitoylphosphatidylcholine (DPPC), hydrogenated soybean phosphatidylcholine (HSPC), cholesterol and distearylphosphatidylethanolamine (DSPE)-methoxypolyethylene glycol (PEG), for example PEG2000 (DSPE-PEG2000).

In a particular embodiment, the molar ratio of the previously identified compounds is preferably 100:50:30:6 or 100:33:27:7.

Another preferred thermosensitive lipidic membrane comprises dipalmitoylphosphatidylcholine (DPPC), monopalmitoylphosphatidylcholin (MPPC) and distearylphosphatidylethanolamine (DSPE)-methoxypolyethylene glycol (PEG), for example methoxypolyethylene glycol-2000 (DSPE-PEG2000).

In a particular embodiment, the molar ratio of the previously identified compounds is preferably 100:12:5.

Another preferred thermosensitive lipidic membrane comprises dipalmitoylphosphatidylcholine (DPPC), monostearylphosphatidylcholine (MSPC), and distearylphosphatidylethanolamine (DSPE)-methoxypolyethylene glycol (PEG), for example methoxypolyethylene glycol-2000 (DSPE-PEG2000).

In a particular embodiment, the molar ratio of the previously identified compounds is preferably 100:12:5.

Depending on the mode of preparation, the size and the degree of lamellarity of the vesicles can be tuned. Several methods for preparing unilamellar lipidic vesicles have been described in the literature: reverse phase evaporation (Szoka et al., PNAS, 1978, 75(9):4191-4198), ethanol injection (Pons et al. International Journal of Pharmaceutics, 1993, 95(1-3):51-56), and heating (Mozafari et al., Journal of Biotechnology, 2007, 129:604-613), but the most simple is the lipid film hydration method (Bangham et al., J. Mol. Biol., 1965, 13:238-252).

Briefly, in the lipid film hydration method, lipids are solubilized in an organic solvent such as chloroform. After homogenization of the solution, the organic solvent is evaporated under a nitrogen stream. The as-obtained dried lipid film is then hydrated by an aqueous medium at a temperature above the main phase transition temperature $T_m$, leading to the formation of multilamellar vesicles with sizes ranging from 100 to 800 nm (Mills J. K. et al., Methods in Enzymology, 2004, 387:82-113). Cycles of dehydration and rehydration, by respectively freezing (in liquid nitrogen) and thawing (at a temperature above $T_m$) the solution, allow the increase of the aqueous internal volume by forming unilamellar vesicles. A process allowing vesicle size calibration is then applied to obtain a homogeneous size distribution. Sonication produces Small Unilamellar Vesicles (SUV) with sizes ranging from 20 to 50 nm, whereas an extrusion process through a filter membrane produces Large Unilamellar Vesicles (LUV) with sizes ranging from 50 to 500 nm, depending on the size of the filter pores. Both processes, sonication and extrusion, have to be performed at a temperature above $T_m$.

The largest size of the thermosensitive liposomes according to the present invention is typically comprised between 50 and 500 nm, preferably between 50 and 250 nm, for example between about 50 nm and about 150 nm.

Thermosensitive liposomes used in the present invention preferably comprise a biocompatible coating to ensure or improve their biocompatibility and specific biodistribution.

The biocompatible coating allows or favours the liposomes' stability in a biocompatible suspension, such as a physiological fluid (blood, plasma, serum, etc.), or any isotonic media or physiological media, for example media comprising glucose (5%) and/or NaCl (0.9%), which is required for pharmaceutical administration.

Such a biocompatible coating is obtained by treating the liposome with a surface treating agent.

Stability may be confirmed by dynamic light scattering of the liposomes in a biocompatible suspension.

Said coating advantageously preserves the integrity of the liposome in vivo, ensures or improves its biocompatibility, and facilitates its optional functionalization (for example with spacer molecules, biocompatible polymers, targeting agents, proteins, etc.).

The coating can be non-biodegradable or biodegradable. Both options can be used in the context of the present invention.

Examples of non-biodegradable coatings are one or more materials or surface treating agents selected from the group consisting of sugar (agarose, for example) and saturated carbon polymers (polyethylene oxide, for example), reticulated or not, modified or not (polymethacrylate or polystyrene, for example), as well as combinations thereof.

Examples of biodegradable coatings are, for example, one or more materials or surface treating agents selected from the group consisting of a biological molecule, modified or not, natural or not, and a biological polymer, modified or not, of natural shape or not. The biological polymer may be a saccharide, an oligosaccharide or a polysaccharide, polysulfated or not, for example, dextran.

The aforementioned materials, compounds or surface treating agents can be used alone or in combinations, mixtures or assemblies, composite or not, covalent or not, optionally in combination with other compounds.

Thermosensitive liposomes according to the present invention can further comprise a surface component enabling specific targeting of biological tissues or cells. Such a surface component is preferably a targeting agent allowing the liposomes' interaction with a recognition element present on the target biological structure.

Such targeting agents can act only once the liposomes are accumulated in the tumor.

As the conformation of the targeting agent is responsible for its interaction with the target, the density of said targeting agent is to be controlled carefully according to methods known by the skilled person. A high density thereof can indeed perturb the targeting agent's conformation and in consequence its recognition by the target cell (see, for example, J. A. Reddy et al., Gene Therapy, 2002, 9:1542; Ketan B. Ghaghada et al., Journal of Controlled Release, 2005, 104:113). In addition, a high target agent density may favour liposomes' clearance by the reticuloendothelial system (RES) during circulation in the vasculature.

The targeting agent may be selected from an antigen, a spacer molecule, and a biocompatible polymer. The targeting agent can be any biological or chemical structure displaying affinity for molecules present in the human or animal body. For instance it can be a peptide, oligopeptide or polypeptide, a protein, a nucleic acid, a hormone, a vitamin, an enzyme and the like, and in general any ligand of molecules (for example, receptors, markers, antigens, etc.). Ligands of molecules are expressed by pathological cells, in particular ligands of tumor antigens, hormone receptors, cytokine receptors or growth factor receptors. Said targeted agents can be selected, for example, from the group consisting of LHRH, EGF, a folate, anti-B—FN antibody, E-selectin/P-selectin, anti-IL-2Rα antibody, GHRH, etc.

The coating can also contain different functional groups (or linker segments), allowing any molecule of interest to bind to the surface of the liposome, such as a surface component enabling specific targeting of biological tissues or cells.

The term "nanoparticle" refers to a particle or aggregate of particles, said nanoparticle comprising a core (or central core) and a coating, the largest dimension of the core being less than about 100 nm. Typically, the largest dimension of the core of the nanoparticle is the diameter of a nanoparticle of round or spherical shape, or the longest length of a nanoparticle of ovoid or oval shape.

The terms "size of the nanoparticle" and "largest size of the nanoparticle" herein refer to the "largest dimension of the core of the nanoparticle".

The "core" can designate a single particle (crystal or crystallite) or an aggregate of particles (aggregate of crystals or crystallites).

Figure 2:
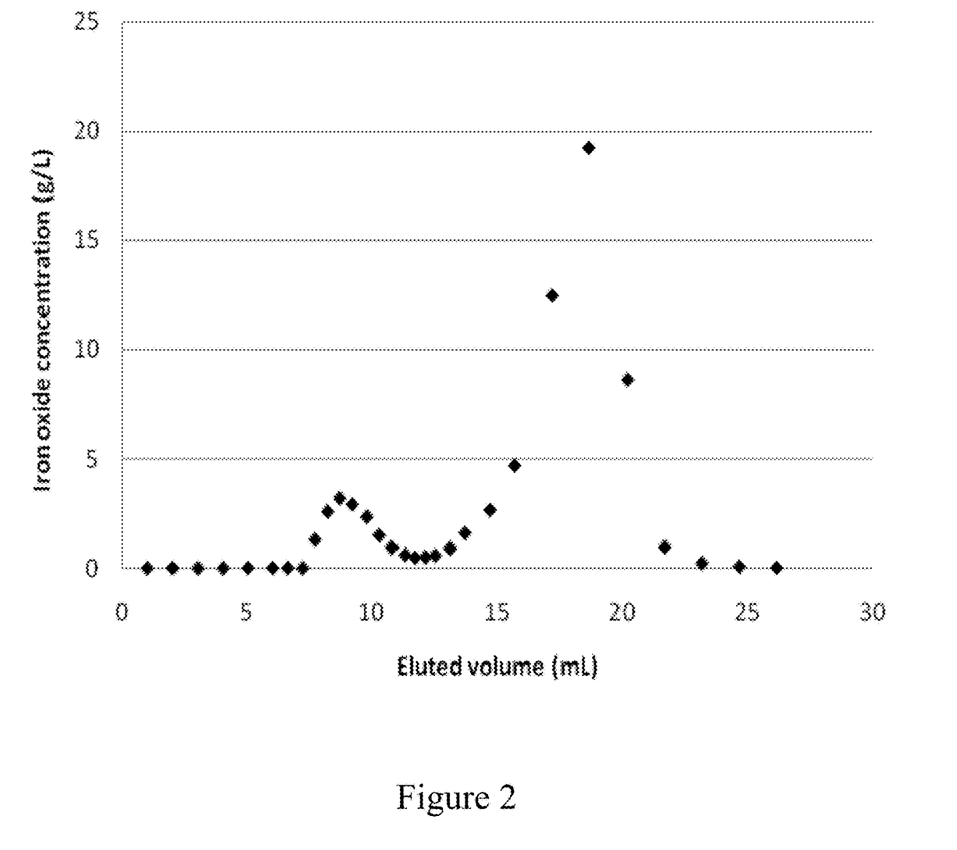
FIG. 2: Typical elution profile obtained for iron oxide-containing liposomes.

Transmission Electron Microscopy (TEM) or cryo-TEM can be advantageously used to measure the size of the core of the nanoparticle, especially when the core consists of a single particle (see FIG. 2). Also, Dynamic Light Scattering (DLS) can be used to measure the hydrodynamic diameter of the core of the nanoparticle in solution when said core consists of a particle or an aggregate of particles. These two methods may further be used one after the other to compare size measurements and confirm said size.

The material is an inorganic material.

The electronic surface charge of the herein-used nanoparticles is below −15 mV or above +15 mV, for example between −15 mV and −20 mV or between +15 mV and +20 mV, typically below −20 mV or above +20 mV, when determined by zeta potential measurements, performed on nanoparticle suspensions with concentrations varying between 0.2 and 8 g/L, nanoparticles being suspended in an aqueous medium at a pH comprised between 6 and 8.

The nanoparticle's shape can be, for example, round, flat, elongated, spherical, ovoid or oval, and the like. The shape can be determined or controlled by the method of production, and adapted by the person of the art according to the desired applications.

As the shape of the particles can influence their "biocompatibility" once delivered to the targeted site, particles having a quite homogeneous shape are preferred. For pharmacokinetic reasons, nanoparticles that are essentially spherical, round or ovoid in shape are thus preferred. Spherical or round shape is particularly preferred.

The largest size of the nanoparticles, i.e., the largest dimension of the core of the nanoparticles, used in the context of the present invention is typically comprised between 1 and 50 nm.

It is advantageously comprised between about 2 nm and about 50 nm, for example between about 2 nm and 30 nm or between about 2 nm and about 20 nm, preferably between about 2 nm and about 10 nm, typically between about 5 nm and about 10 nm, between about 4 nm and about 8 nm or between about 30 nm and 50 nm.

The nanoparticles used in the context of the present invention comprise a core and a coating, said coating being responsible for the presence of an electrostatic surface charge below −20 mV or above +20 mV when measured in an aqueous medium at physiological pH.

The electrostatic coating is advantageously a "fill coating" (complete monolayer). This implies the presence of a very high density of molecules creating an appropriate and homogeneous charge on the all surface of the nanoparticle.

The coating can be an inorganic or organic surface coating.

When inorganic, the coating may be selected from the group consisting of an oxide, a hydroxide, and an oxyhydroxide. The inorganic coating may comprise, for example, silicium, aluminum, calcium and/or magnesium.

An inorganic agent selected from the group consisting of, for example, magnesium and calcium will bring a positive charge (above +20 mV) to the surface of the nanoparticle at pH 7.

In another embodiment, a silicium group may be used to bring a negative charge (below −20 mV) to the surface of the nanoparticle at pH 7.

When organic, the coating is prepared with a molecule capable of interacting, through covalent binding or electrostatic binding, with the nanoparticle's surface and of giving surface properties to said nanoparticle.

The surface coating organic molecule has two groups, R and X. The function of X is to interact with the nanoparticle's surface and the function of R is to give the nanoparticle's surface its specific properties.

X may be selected for example from a carboxylate (R—COO$^-$), a silane (R—Si(OR)$_3$), a phosphonic (R—PO(OH)$_2$), a phosphoric (R—O—PO(OH)$_2$), a phosphate (R—PO$_4^{3-}$) and a thiol (R—SH) group.

R brings at least the electronic surface charge to the nanoparticle in an aqueous suspension at a physiological pH.

When R brings a positive charge to the nanoparticle's surface, R may be an amine (NH$_2$—X).

When R brings a negative charge to the nanoparticle's surface, R may be a phosphate (PO$_4^{3-}$—X) or a carboxylate (COO$^-$—X).

Organic coating conferring a positive charge (above +20 mV) to the nanoparticle's surface may be selected from, for example, aminopropyltriethoxisilane, polylysine or 2-aminoethanethiol.

Organic coating conferring a negative charge (below −20 mV) to the nanoparticle's surface may be selected from, for example, a polyphosphate, a metaphosphate, a pyrophosphate, etc., or, for example, from citrate or dicarboxylic acid, in particular succinic acid.

Again, the electrostatic coating is advantageously a "full coating".

This electrostatic coating and especially amino or carboxylic moieties can further be used to link any group or agent on the nanoparticle's surface.

Optionally, the nanoparticle's surface can be functionalized using a steric group. Such a group may be selected from polyethylene glycol (PEG), polyethylenoxide, polyvinylalcohol, polyacrylate, polyacrylamide (poly(N-isopropylacrylamide)), polycarbamide, a biopolymer or polysaccharide such as Dextran, Xylan, cellulose, or collagen, and a zwitterionic compound such as polysulfobetain.

This steric group increases the nanoparticle's stability in a biocompatible suspension, such as a physiological fluid (blood, plasma, serum, etc.) or any isotonic media or physiological media, for example media comprising glucose (5%) and/or NaCl (0.9%).

The inorganic material constituting the core is a superparamagnetic material.

Superparamagnetic materials include, for example, iron, nickel, cobalt, gadolinium, samarium, neodymium, preferably in the form of an oxide, a hydroxide or a metal, and any mixture thereof.

In specific examples, the material forming the core is selected from the group consisting of ferrous oxide and ferric oxide. In a preferred embodiment of the present invention, the oxide nanoparticles are made of magnetite or maghemite.

Mixed materials can also be used to optimize interactions between a magnetic field and nanoparticles. Solid solution forms (well-known by one skilled in the art as random mixtures of several materials) such as CoFe$_2$O$_4$ can be used as a mixed material. Solid solution forms in demixed phases, such as Fe$_2$O$_3$/Co, can further be used.

Products of interest in the context of the present invention include any compound (for example a drug) with therapeutic or prophylactic effects. It can be a compound that affects or participates in tissue growth, cell growth, or cell differentiation, a compound that is able to invoke a biological action such as an immune response, or a compound that can play any other role in one or more biological processes.

A non-limiting list of examples includes antimicrobial agents (including anti bacterial agents, in particular antibiotics, antiviral agents and anti-fungal agents); anti-tumor agents, in particular anticancer chemotherapeutic agents such as cytostatic(s) and cytotoxic(s), and any other biological or inorganic product intended to treat cancer, such as a therapeutic nucleic acid, in particular a micro RNA (miRNA), a short-hairpin RNA (shRNA) and/or a small interfering RNA (siRNA).

Drugs in the present invention can also be prodrugs.

Any combination of such products of interest may further be used.

The compound(s) of interest may be present in the inner, the outer, or both of the compartments of the carrier, e.g., in the cavity and/or in the shell of a liposome.

The present disclosure further provides kits comprising any one or more of the herein-described thermosensitive liposomes comprising superparamagnetic nanoparticles and a compound of interest to be delivered and released at a target site, or compositions comprising such liposomes. For example, the kit comprises at least one thermosensitive liposome or population of thermosensitive liposomes as herein described and also one or more containers filled with one or more of the ingredients of the diagnostic compositions described herein.

A labeling notice providing instructions for using the products can further be provided for using the thermosensitive liposome, population of thermosensitive liposomes, or compositions according to the present methods of the invention.

Other aspects and advantages of the invention will become apparent in the following examples, which are given for purposes of illustration and not by way of limitation.

EXPERIMENTAL SECTION

Example 1: Preparation of 5 nm-Sized Nanoparticles

Iron oxide nanoparticles with a size distribution centered on 5 nm are synthesized by coprecipitation of ferrous and ferric ions adapted from U.S. Pat. No. 4,329,241 and Bacri et al. (J. Magn. Mat., 1986, 62:36-46).

Briefly, the reacting medium, with controlled ionic strength, consists of a solution of sodium nitrate 3M maintained at pH 12. A 3M sodium nitrate solution of ferrous and ferric ions in a molar ratio Fe(III)/Fe(II) equal to 2 is prepared and slowly added to the reacting medium under mixing. It rapidly turns black. The whole solution is then aged for one night at ambient temperature under mixing.

Ferrite nanoparticles are then sedimented on a magnet and the supernatant is removed in order to eliminate the reacting medium. Then peptization (acidification) and oxidation of the nanoparticles' surface is performed by diluting the pellet in a solution of nitric acid ($HNO_3$) 2M at room temperature under vigorous mixing.

Oxidation of the nanoparticles' cores is performed by incubation of the pellet in a solution of ferric nitrate at an elevated temperature (>90° C.) under vigorous mixing.

The nanoparticles are then washed by centrifugation.

The pellet is finally diluted in acidic water in order to reach a concentration of 150 g/L in iron oxide. The solution is homogenized by sonication and the pH is then adjusted to pH 2.

Figure 1:
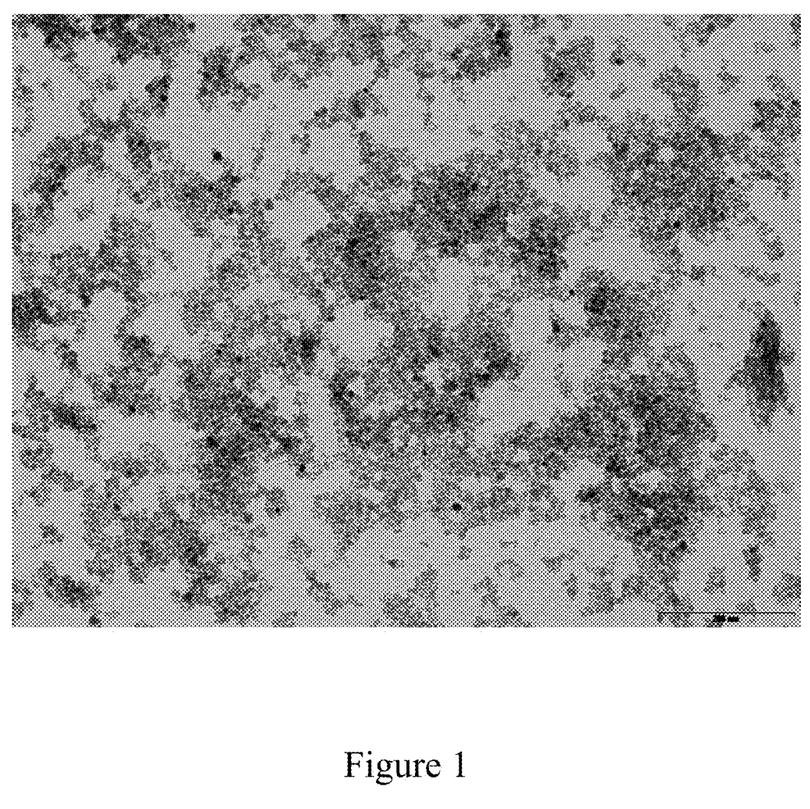
FIG. 1: TEM observations of 5 nm-sized iron oxide nanoparticles (scale bar=200 nm).

The morphology (size and shape) of nanoparticles was observed by Transmission Electron Microscopy (FIG. 1). The crystalline structure of iron oxide nanoparticles was confirmed by X-ray diffraction analysis.

Example 2: Surface Treatment of Nanoparticles—Functionalization of Nanoparticles with Sodium Hexametaphosphate (HMP)

A suspension of sodium hexametaphosphate is added to the suspension of iron oxide nanoparticles from example 1 (the amount of sodium hexametaphosphate added being below LD50/5) and the pH of the suspension is adjusted to a pH comprised between 6 and 8 Electronic surface charge (<−20 mV) is determined by zeta potential measurements on a Zetasizer NanoZS (Malvern Instruments), using a 633 nm HeNe laser, performed on nanoparticle suspensions with concentrations varying between 0.2 and 2 g/L, the nanoparticles being suspended in an aqueous medium at a pH comprised between 6 and 8.

Example 3: Co-Encapsulation of Iron Oxide Nanoparticles and Doxorubicin Inside Liposomes 3.1 Preparation of Thermosensitive Liposomes (TLS) Encapsulating Iron Oxide Nanoparticles The thermosensitive liposomes encapsulating iron oxide nanoparticles are prepared using the lipidic film re-hydration method (Bangham et al., J. Mol. Biol., 1965, 13:238-252; Martina et al., J. Am. Chem. Soc., 2005, 127:10676-10685):

a) Lipids are solubilized in chloroform. Chloroform is finally evaporated under a nitrogen flow. Re-hydration of the lipidic film is performed at 55° C. with 2 mL of the iron oxide solution described in Example 2, so that the lipidic concentration is 50 mM.

The following lipidic composition was used: dipalmitoylphosphatidylcholine (DPPC), hydrogenated soybean phosphatidylcholine (HSPC), cholesterol (Chol) and pegylated distearylphosphatidylethanolamine (DSPE-PEG2000) in the molar ratio 100:33:27:7 (DPPC:HSPC:Chol:DSPE-PEG2000).

b) Freeze-thaw cycles are then performed 20 times, by successively plunging the sample into liquid nitrogen and into a water bath regulated at 55° C.

c) A thermobarrel extruder (LIPEX™ Extruder, Northern Lipids) was used to calibrate the size of the nanoparticle-containing liposomes under controlled temperature and pressure. In all cases, extrusion was performed at 55° C., under a pressure ranging from 2 to 20 bars.

d) Separation of non-encapsulated particles is performed by size exclusion chromatography on a Sephacryl S1000 filtration gel.

e) Elution profile is determined by quantification of magnetic nanoparticles by UV-visible spectroscopy (Cary 100 Varian spectrometer) via a ferrous ions/phenanthroline colorimetric reaction (FIG. 2) adapted from Che et al., Journal of Chromatography B, 1995, 669:45-51 and Nigo et al., Talanta, 1981, 28:669-674. Liposome-containing fractions are collected (FIG. 2, first peak). The concentration of iron oxide in the liposomes ranges from 1 to 2.5 g/L. $T_m$ of the composition is 43° C.

3.2 Loading of Thermosensitive Liposomes (TLS) Encapsulating Iron Oxide Nanoparticles with Doxorubicin An active loading of doxorubicin (DOX) inside iron oxide-containing liposomes was used, via pH gradient. Once trapped in the internal aqueous cores of the liposomes, doxorubicin leakage is prevented by complexation of the anthracycline molecule with an ammonium salt:

a) Iron oxide-containing liposomes (prepared as explained in example 3.1) are incubated in a solution of ammonium hydrogen phosphate $((NH_4)_2HPO_4)$ 120 mM, at a pH around 5 for 1 hour.

b) Dialysis steps are performed in HEPES buffer saline (HEPES 20 mM, NaCl 140 mM, pH 7.4) to eliminate external $(NH_4)_2HPO_4$: once over 1 night at 4° C., then twice for 3 h at ambient temperature (final dilution factor of 250*250*250).

c) 284 μL of a doxorubicin stock solution at 7 mg/mL in NaCl 140 mM is added to 1 mL of iron oxide-containing liposome solution to obtain a doxorubicin concentration of 1.55 mg/mL. The composition is incubated for 1 night at 37° C.

d) Non-encapsulated doxorubicin is then eliminated by size-exclusion chromatography on a Sephadex G50 filtration gel (column height: 5 cm; eluant: HEPES buffer saline). The volume of doxorubicin-loaded liposomes deposited onto the gel is 700 μL. Fractions of 500 μL are collected.

e) Elution profile is performed by quantifying doxorubicin concentration in each fraction (by measurement of absorbance at 480 nm). Liposomes/doxorubicin-containing fractions are collected.

f) Final liposomal doxorubicin concentration is determined by measuring absorbance of doxorubicin at 480 nm by UV-visible spectroscopy.

3.3 Preparation of "Non-Thermosensitive Liposomes" (NTSL) Encapsulating Iron Oxide Nanoparticles The previously described procedure (see example 3.1) was followed except that, in step a), the following lipidic composition was used: hydrogenated soybean phosphatidylcholine (HSPC), cholesterol (Chol) and pegylated distearylphosphatidylethanolamine (DSPE-PEG2000) in the molar ratio 100:65:7 (HSPC:Chol:DSPE-PEG2000).

In steps a), b) and c), the re-hydration of the lipidic film, thaw cycles and extrusion process are performed at 62° C.

Figure 3:
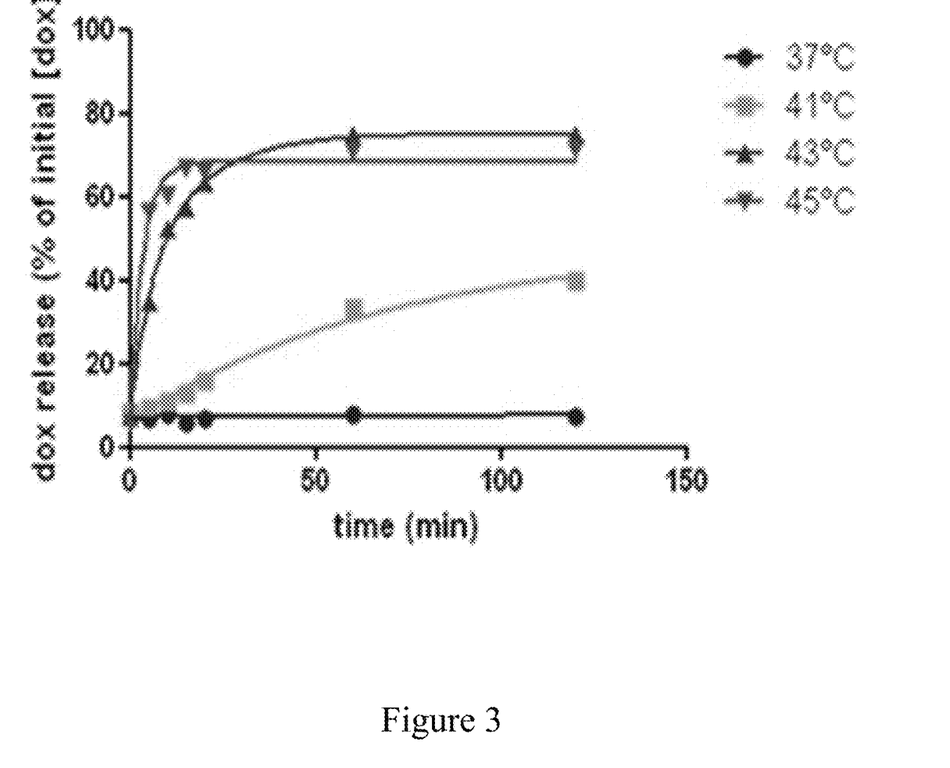
FIG. 3: Release profile of doxorubicin.

Example 4: Kinetics of Drug Release from Thermosensitive Liposomes Encapsulating Both Doxorubicin and Iron Oxide Nanoparticles FIG. 3 shows the release kinetics profile of doxorubicin (DOX)-loaded iron oxide-containing thermosensitive liposomes (TSL) as prepared in example 3.2. Doxorubicin release, as a function of temperature and time, is determined by fluorescence measurements.

The doxorubicin release profile is characterized using the autoquenching properties of doxorubicin (Jeffrey K. Mills et al., Biochimica et Biophysica Acta, 2005, 1716:77-96). Briefly, fluorescence intensity is quenched when DOX is highly concentrated inside liposomes, but increases when DOX is released and then diluted in the external medium.

Fluorescence measurements are performed with a Cary Eclipse (Varian) spectrophotometer with $\lambda_{excitation}$=480 nm and $\lambda_{emission}$=590 nm. Liposomes are diluted 200 times in phosphate buffer saline (PBS) supplemented with 50% volume fetal bovine serum (FBS). Initial fluorescence intensity $I_0$ was measured at time t=0 and at $T_0$=25° C. The diluted samples are plunged in a water bath to reach temperature T (37° C., 41° C., 43° C., 45° C.). At different time points, a sample is collected and plunged in an ice bath to reach the initial temperature ($T_0$). The fluorescence intensity $I_{released}$ is then measured. 0.1% volume of Triton TX100 (10% vol in distilled water) is then added in order to break apart the lipidic membrane to obtain $I_{total}$ corresponding to the total amount of doxorubicin. The external % of DOX present at t=0 and $T_0$=25° C. is calculated as $I_0/I_{total}$ and the released % of DOX (function of temperature) is calculated as $I_{released}/I_{total}$.

As shown in FIG. 3, release of doxorubicin is maximal when the thermosensitive liposome solution is heated above 43° C. (this corresponds to Tm which is the main gel-to-liquid crystalline phase transition temperature of this liposome composition). At this temperature the lipidic membrane is in a fluid state and its permeabilization allows for the release of the drug out of the liposome.

Example 5: MRI Monitoring of Membrane Permeabilization (and Subsequent Drug Release) of Thermosensitive Liposomes Encapsulating Iron Oxide Nanoparticles Upon Heating at or Above Tm Determination of $r_1$ and $r_{2*}$ relaxivities was done thanks to measurements of relaxation times T1 and T2* performed on a 1.5 Tesla clinical MRI Philips Achieva, using a head SENSE coil, for thermosensitive liposomes (TSL) (example 3.1) and non-thermosensitive liposomes (NTSL) (example 3.3), both loaded with 5 nm-sized iron oxide nanoparticles, and for non-encapsulated iron oxide nanoparticles (free NP) (example 1). A range of dilution for each sample was performed corresponding to 40, 20, 10 and 5 μg/mL in iron oxide, respectively. Dilutions were performed in agarose gel (4%). Samples were heated using a water bath first at 37° C. and then at 45° C., and relaxation times T1 and T2* of each dilution were measured at 37° C. and at 45° C.

For $T_1$ measurements, inversion recovery sequences were used (TR/TI first/ΔTI=2000/50/100 ms, TE=10 ms, NEX=2, FOV=(1×1×3 mm)$^3$, matrix=128×168, with TR=repetition time, IT=inversion time, TE=echo time, NEX=number of excitations, FOV=field of view.

Fast gradient echo sequences were used for $T_{2*}$ measurement, with flip angle=40°, 10 echoes, TR/TE first/ΔTE=300/10/10 ms, NEX=4.

Figure 4A:
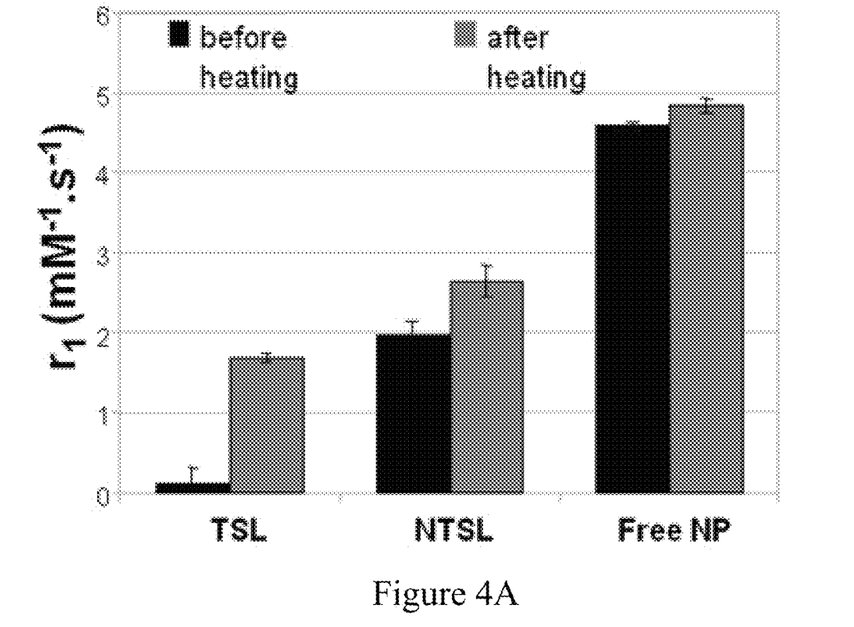
FIGS. 4A-4B: Evolution upon heating of Magnetic Resonance (MR) relaxivities at 1.5 Tesla of iron oxide nanoparticles encapsulated in thermosensitive (TSL) and non-thermosensitive liposomes (NTSL), and free nanoparticles (free NP).
Figure 4B:
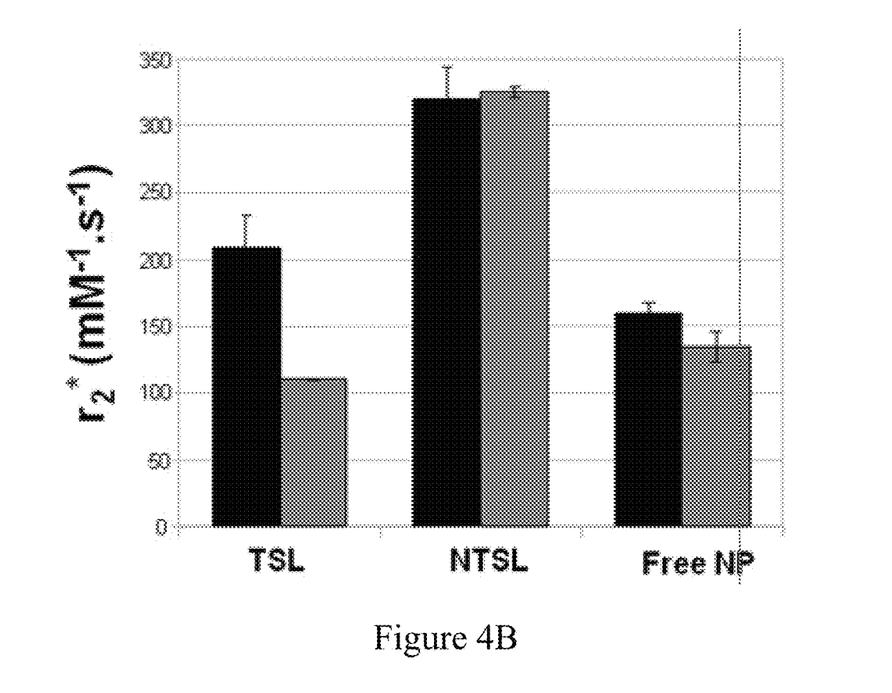

FIG. 4 shows the modification of relaxivity values $r_1$ (FIG. 4A) and $r_{2*}$ (FIG. 4B) upon heating at 45° C. corresponding to a temperature above the main gel-to-liquid crystalline phase transition temperature Tm (at this temperature the lipidic membrane is then in a fluid state).

Non-encapsulated iron oxide nanoparticles (free NP) and iron oxide-loaded NTSL demonstrated no significant evolution of the longitudinal relaxivity $r_1$ before and after heating at 37° C. and 45° C. respectively. In contrast, the longitudinal relaxivity $r_1$ of iron oxide-loaded TSL presents a 10-fold increase upon heating (from $r_1$=0.1 mM$^{-1}$·s$^{-1}$ at 37° C. to $r_1$=1.68 mM$^{-1}$·s$^{-1}$ at 45° C.).

Non-encapsulated iron oxide nanoparticles (free NP) and iron oxide-loaded NTSL demonstrated no significant evolution of the transverse relaxivity $r_{2*}$ before and after heating at 37° C. and 45° C. respectively. In contrast, the transverse relaxivity $r_{2*}$ of iron oxide-loaded TSL is decreased by about 2-fold upon heating (from $r_{2*}$=208.7±23.4 mM$^{-1}$·s$^{-1}$ at 37° C. to $r_{2*}$=109.4±0.2 mM$^{-1}$·s$^{-1}$ at 45° C.).

This example demonstrates the influence of the permeabilization of the lipidic membrane of TSL on the longitudinal and transverse relaxation times of protons in the environment of nanoparticles. This phenomenon is well highlighted by presenting the results as an evolution of the ratio $r_{2*}/r_1$ (see Table 1) before and after heating of the thermnosensitive liposome solution above Tm.

TABLE 1

Evolution of the ratio $r_2*/r_1$ upon heating for TSL, NTSL and free NP

| Temperature (° C.) | TSL | NTSL | Free NP |
|---|---|---|---|
| 37° C. | 1000 | 150 | 33 |
| 45° C. | 67 | 128 | 28 |
| k(*) | 15 | 1.2 | 1.2 |

(*)k represents the ratio between $r_2*/r_1$ values at 37° C. and 45° C. respectively.

A surprisingly marked decrease of $r_{2*}/r_1$ values upon heating is demonstrated for TSL, whereas no significant evolution for NTSL and free NP is observed (see k value).

Figure 5:
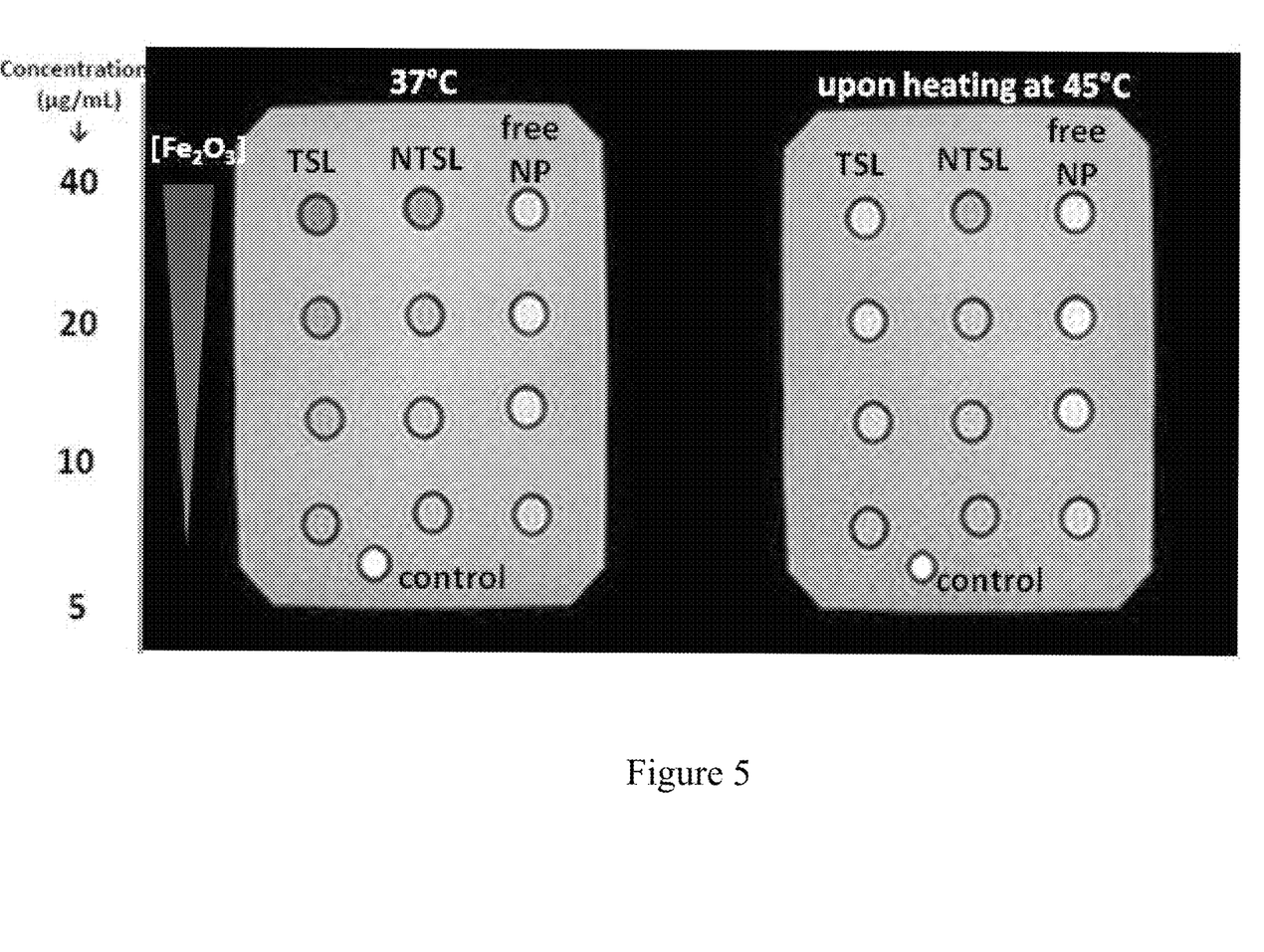
FIG. 5: Evolution upon heating of Magnetic Resonance (MR) signal at 1.5 Tesla of iron oxide encapsulated in thermosensitive (TSL) and non-thermosensitive liposomes (NTSL), and free nanoparticles (free NP).

FIG. 5 shows MR imaging of iron oxide-containing samples (TSL, NTSL and free nanoparticles) for different dilutions factors (40, 20, 10 and 5 μg/mL in iron oxide). The experiment was performed on a Philips Achieva 1.5 Tesla, using a fast gradient echo sequence (TR/TE=300/10 ms, NEX=4, FOV=(1×1×3 mm)³, matrix=128× 168, flip angle=40°). For a concentration in iron oxide of 40 μg/mL, the modification of MRI contrast for thermosensitive liposome (TSL) is clearly visible upon heating: a "hyposignal" is observed at 37° C. whereas a "hypersignal" is obtained at 45° C. No significant signal variation was observed on both non-thermosensitive liposomes (NTSL) and iron oxide nanoparticles (free NP).

This major modification of the ratio $r_{2*}/r_1$ upon heating at a temperature above Tm constitutes a highly sensitive "probe" of the permeabilization of the lipidic membrane of liposomes. The subsequent drug release that occurs when a drug is co-encapsulated with the iron oxide nanoparticles inside the liposome (see example 4.1) can be monitored via detection of this marked MRI signal modification.

Furthermore, monitoring of lipidic membrane permeabilization of the thermosensitive liposomes may be observed by a T2*-mapping prior and after heating of the thermosensitive liposome solution at or above Tm.

Figure 6:
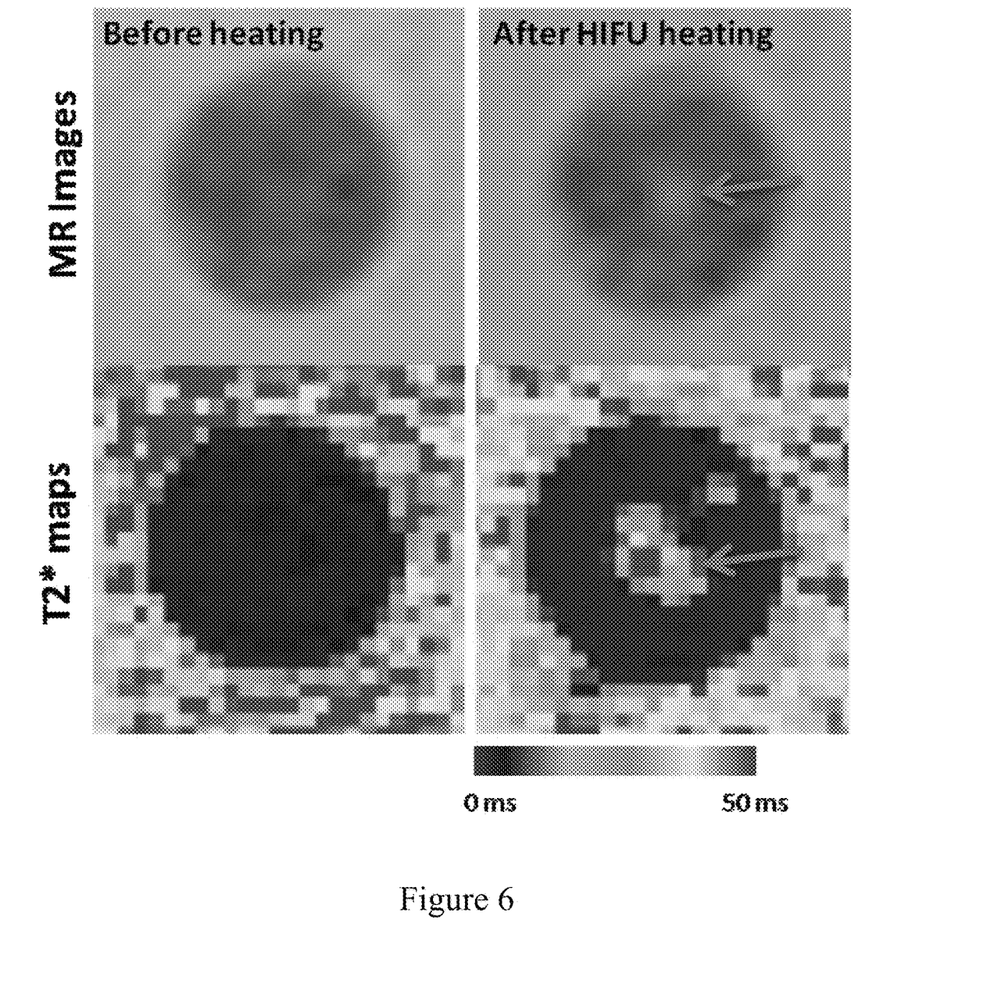
FIG. 6: MR signal and T2*-mapping of iron oxide nanoparticles encapsulated in thermosensitive liposomes (TSL) before and after High Intensity Focused Ultrasound (HIFU)-induced heating.

In FIG. 6, ultrasound experiments were performed with an in-house-designed, single-channel focused ultrasound transducer (Imasonic SA) incorporated in the bed of the 1.5-T MRI system. The transducer has a focal length of 80 mm, with a sinusoidal signal of 1.5 MHz. Heating was performed with acoustic power of 20 W for 60 seconds.

TSL containing iron oxide nanoparticles (20 μg/ml), included in agarose gel (4%-2% silica), were used.

Upon heating, thermosensitive liposomes showed punctual MR signal and $T_2^*$ relaxation time enhancement, with variations clearly visible at the HIFU focal point (red arrow). On average, the positive enhancement was of about 51%. Before heating. $T_{2*}$ was 4.9±0.4 ms, and increased to 54±31.4 ms after HIFU heating (red arrow).

The result demonstrates that real-time imaging of drug release is now possible.

We claim:

1. A method of monitoring a liposome membrane permeabilization and the incidental release of a product of interest encapsulated in the liposome, wherein the liposome comprises a thermosensitive lipidic membrane encapsulating the product of interest and superparamagnetic nanoparticles, the superparamagnetic nanoparticles having an electrostatic surface charge below −20 mV or above +20 mV when measured in an aqueous medium between pH 6 and 8, and wherein the method comprises:
   a) measuring T2* allowed by the superparamagnetic nanoparticles,
   b) heating the liposome at phase transition temperature (Tm) or above Tm,
   c) measuring T2* allowed by the superparamagnetic nanoparticles after step b),
   d) obtaining the transverse relaxivity ($r_{2*}$) values from the T2* values obtained from step a) and step c), and
   e) determining the ratio of $r_{2*}$ before the heating step at Tm or above Tm/$r_{2*}$ after the heating step at Tm or above Tm, a ratio above 1.5 being indicative of the liposome membrane permeabilization and of the incidental release of the product of interest, thereby monitoring the liposome membrane permeabilization.

2. The method according to claim 1, wherein the method further comprises at least one step of measuring T2*, or T2 and T2* allowed by the superparamagnetic nanoparticles, during the heating step b).

3. The method according to claim 1, wherein Tm is between 39° C. and 45° C.

4. The method according to claim 1, wherein the thermosensitive lipidic membrane comprises at least a phosphatidylcholine.

5. The method according to claim 4, wherein the thermosensitive lipidic membrane further comprises cholesterol.

6. The method according to claim 4, wherein the thermosensitive lipidic membrane further comprises distearylphosphatidylethanolamine-methoxypolyethylene glycol.

7. The method according to claim 5, wherein the thermosensitive lipidic membrane further comprises distearylphosphatidylethanolamine-methoxypolyethylene glycol.

8. The method according to claim 1, wherein the largest size of the liposome is between 50 and 500 nm.

9. The method according to claim 1, wherein the nanoparticles are covalently or electrostatically fully coated with an agent selected from a carboxylic acid, a phosphate and an amine.

10. The method according to claim 1, wherein the nanoparticles are prepared from an iron oxide selected from magnetite and/or maghemite.

11. The method according to claim 1, wherein the nanoparticle largest size is between 2 and 30 nm.

12. The method according to claim 1, wherein the product of interest is selected from a therapeutic nucleic acid, a cytostatic compound, and a cytotoxic compound.

13. The method according to claim 1, wherein said thermosensitive lipidic membrane comprises dipalmitoylphosphatidylcholine (DPPC), hydrogenated soybean phosphatidylcholine (HSPC), cholesterol and distearylphosphatidylethanolamine (DSPE)-methoxypolyethylene glycol (PEG) in a molar ratio of 100:50:30:6 or 100:33:27:7.

14. The method according to claim 1, wherein said thermosensitive lipidic membrane comprises dipalmitoylphosphatidylcholine (DPPC), monopalmitoylphosphatidylcholine (MPPC) and distearylphosphatidylethanolamine (DSPE)-methoxypolyethylene glycol (PEG) in a molar ratio of 100:12:5.

15. The method according to claim 1, wherein said thermosensitive lipidic membrane comprises dipalmitoylphosphatidylcholine (DPPC), monostearylphosphatidylcholine (MSPC), and distearylphosphatidylethanolamine (DSPE)-methoxypolyethylene glycol (PEG) in a molar ratio of 100:12:5.

16. The method according to claim 1, wherein the method consists of:
   a) measuring T2* allowed by the superparamagnetic nanoparticles,
   b) heating the liposome at phase transition temperature (Tm) or above Tm,
   c) measuring T2* allowed by the superparamagnetic nanoparticles after step b),
   d) obtaining the transverse relaxivity ($r_{2*}$) values from the T2* values obtained from step a) and step c), and
   e) determining the ratio of $r_{2*}$ before the heating step at Tm or above Tm/$r_{2*}$ after the heating step at Tm or above Tm, a ratio above 1.5 being indicative of the liposome membrane permeabilization and of the incidental release of the product of interest, thereby monitoring the liposome membrane permeabilization.

17. A method of monitoring a liposome membrane permeabilization and the incidental release of a product of interest encapsulated in the liposome, wherein the liposome comprises a thermosensitive lipidic membrane encapsulating the product of interest and superparamagnetic nanoparticles, the superparamagnetic nanoparticles having an electrostatic surface charge below −20 mV or above +20 mV when measured in an aqueous medium between pH 6 and 8, and wherein the method consists of:

a) measuring T2* and longitudinal relaxation time (T1) allowed by the superparamagnetic nanoparticles,    b) heating the liposome at Tm or above Tm,    c) measuring T2* and T1 allowed by the superparamagnetic nanoparticles after step b),    d) obtaining $r_{2*}$ and longitudinal relaxivity ($r_1$) values from the T2* and T1 values obtained from steps a) and c), and    e) determining the ratio of $r_{2*}/r_1$ before and after the heating step at Tm or above Tm, a ratio of $r_{2*}/r_1$ before the heating step b) and of $r_{2*}/r_1$ after the heating step b) above 2 being indicative of the liposome membrane permeabilization and of the incidental release of the product of interest, thereby monitoring the liposome membrane permeabilization.

18. The method according to claim 17, wherein the method further comprises at least one step of measuring T2* and T1 allowed by the superparamagnetic nanoparticles, and optionally T2 allowed by the superparamagnetic nanoparticles, during the heating step b).

\* \* \* \* \*

UNITED STATES PATENT AND TRADEMARK OFFICE
CERTIFICATE OF CORRECTION

PATENT NO. : 10,064,962 B2
APPLICATION NO. : 14/886326
DATED : September 4, 2018
INVENTOR(S) : Agnès Pottier et al.

It is certified that error appears in the above-identified patent and that said Letters Patent is hereby corrected as shown below:

In the Specification

Column 16
Line 3, "6 and 8 Electronic" should read --6 and 8 Electronic--.

Signed and Sealed this
Twenty-seventh Day of August, 2019

Andrei Iancu
*Director of the United States Patent and Trademark Office*